United States Patent [19]

Kole

[11] Patent Number: 5,069,669

[45] Date of Patent: Dec. 3, 1991

[54] EXPANDABLE FINGER GUARD FOR A HYPODERMIC NEEDLE CAP

[75] Inventor: Richard L. Kole, New Hempstead, N.Y.

[73] Assignee: Design Opportunity Corp., New City, N.Y.

[21] Appl. No.: 448,674

[22] Filed: Dec. 11, 1989

[51] Int. Cl.⁵ ............................................... A61M 5/00
[52] U.S. Cl. .................................. 604/198; 604/192; 604/263
[58] Field of Search ...................... 604/192, 198, 263

[56] References Cited

U.S. PATENT DOCUMENTS

| | | | |
|---|---|---|---|
| 4,139,009 | 2/1979 | Alvarez | 604/198 |
| 4,573,975 | 3/1986 | Frist et al. | 604/192 |
| 4,654,034 | 3/1987 | Masters et al. | 604/192 |
| 4,735,618 | 5/1988 | Hagen | 604/192 |
| 4,767,412 | 8/1988 | Hymanson | 604/192 |
| 4,781,697 | 11/1988 | Slaughter | 604/192 |
| 4,782,841 | 11/1988 | Lopez | 128/164 |
| 4,935,013 | 6/1990 | Haber et al. | 604/192 |

Primary Examiner—C. Fred Rosenbaum
Assistant Examiner—Corrine Maglione
Attorney, Agent, or Firm—Brooks Haidt Haffner & Delahunty

[57] ABSTRACT

A sleeve with a plurality of contiguous longitudinally oriented strips between end bands is secured at one end to a cap for a hypodermic needle. The sleeve is constructed to bulge radially outwardly when its ends are slid longitudinally toward each other thereby forming a finger guard to protect against needle sticks.

3 Claims, 3 Drawing Sheets

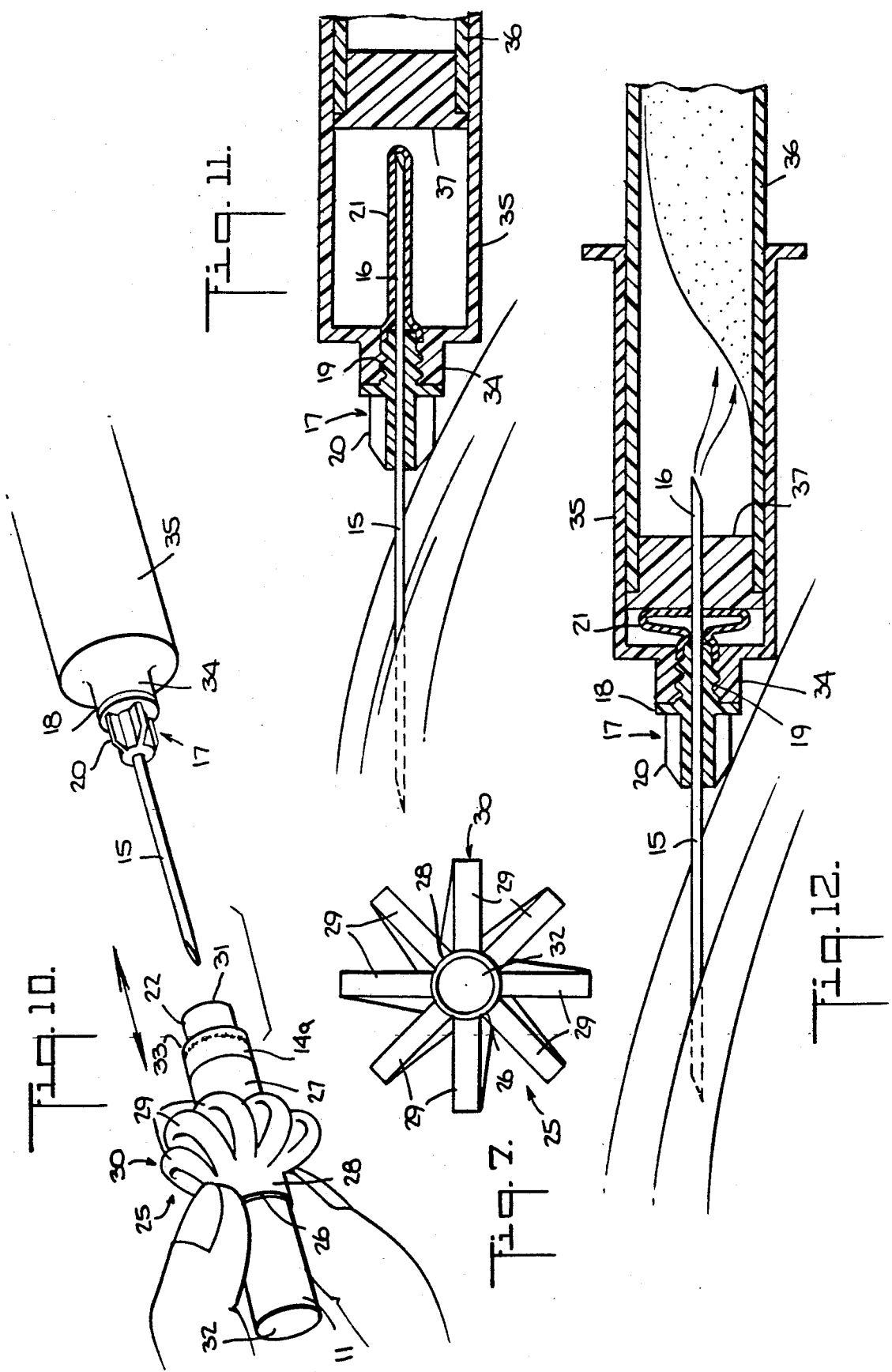

EXPANDABLE FINGER GUARD FOR A HYPODERMIC NEEDLE CAP

BACKGROUND OF THE INVENTION

The present invention relates to the packaging and handling of hollow needles for hypodermic syringes and the like, and, more particularly, to a finger guard for preventing inadvertent and accidental needle sticks.

Hypodermic needles of the type used with an evacuated tube type collection device for obtaining samples of body fluids, particularly blood, are generally supplied in a tripart assembly consisting of a double pointed needle member sealed within two end caps. In use, first one end cap is removed and the exposed needle, usually sheathed in a pierceable self-sealing elastomeric sheath, is assembled to a tube-receiving cylinder. Next, the second needle is uncovered by removing its end cap, usually only about ¼" to 5/16" in diameter, and the exposed needle is inserted in the patient transdermally. The major problem arises after the patient piercing needle is removed from the patient contaminated with body fluid, often carrying contagious disease factors. Accidental needle pricks of the medical attendant in the process of restoring the cap over the needle are not uncommon. Heretofore, various attempts have been made to provide protection to the medical personnel, and the following patents are believed to be illustrative of the state of the prior art.

U.S Pat. No. 4,139,009 discloses a hypodermic needle assembly with a retractable needle cover. In U.S. Pat. No. 4,573,975 a protective shield resembling an umbrella is provided at the neck of a needle container and is supplied folded down against the body of the container held in place by an enveloping cylindrical holder, the "umbrella" erecting when the holder is removed. U.S. Pat. No. 4,654,034 provides funnel shaped guards formed integrally at the end of the needle cap, while U.S. Pat. No. 4,767,412 provides a finger guard in the form of a funnel which is formed separate from but engageable about a needle cap. U.S. Pat. No. 4,781,697 discloses another form of removable shield wherein a dual funnel-shape shield is provided for both needle caps of a double needle assembly Finally, U.S. Pat. No. 4,782,841 provides an assembly with a sleeve that is slidable along a needle which has been provided with a collar attached to the needle at a longitudinally intermediate location which collar, when the sleeve is urged toward the tip end of the needle, engages the sleeve and locks it in a forward needle point guarding position.

The existing constructions that are exemplified by the above-mentioned patents all have one or another disadvantage or draw-back. Where the guard is formed integrally with the cap, whether in folded condition as in U.S. Pat. No. 4,573,975, or in stiffly erected form as in U.S. Pat. No. 4,654,034, the resultant increase in the size of the cap, its bulk, is an undesireable factor. Packaging is enlarged and dispensary storage space requirements are increased. On the other hand, where the guard is a separate item that must be placed over the cap, there is the draw-back that, when personnel are rushed or due to the very nature of the individual involved, the guard will not be used.

SUMMARY OF THE PRESENT INVENTION

It is, therefore, an object of the present invention to provide a finger guard on a cap for a hypodermic needle which guard is always present but, until actual use of the needle, only minimally increases the size of the needle assembly package.

Another object of the present invention is to provide such guard in an economical manner.

In accordance with one aspect of the present invention there is provided a finger guard comprising a tubular element of flexible needle-puncture-resistant material having first and second circumferentially continuous end sections joined by a plurality of longitudinally extending circumferentially contiguous strips which strips, when the end sections are urged axially toward one another, project radially to form an umbrella-like structure.

In accordance with another aspect of the present invention there is provided a finger guard for a double pointed multiple sample hypodermic needle assembly wherein the needle assembly has: a) first and second hollow needles projecting in opposite directions along a common longitudinal axis from an intermediate body structure which body structure has a generally centrally located radial flange, an externally threaded extension on one side of the flange, and a cap-engaging extension on the other side of the flange; b) a first cap enclosing the first hollow needle and engaging the cap engaging extension; and c) a second cap enclosing the second hollow needle and the externally threaded extension and telescoped over the radial flange. The finger guard comprises a tubular element of flexible needle-puncture-resistant material having first and second circumferentially continuous end sections joined by a plurality of longitudinally extending circumferentially contiguous strips which strips, when the end sections are urged axially toward one another, project radially to form an umbrella-like structure. The first end section of the tubular element is secured about and to the first cap in the vicinity of the open end of the first cap with the second end section being axially slidable and rotatable relative to the first cap.

BRIEF DESCRIPTION OF THE DRAWINGS

The invention will be understood better after reading the following detailed description of the presently preferred embodiment with reference to the appended drawings in which:

FIG. 7 is an end elevational view of the needle cap with expanded guard in FIG. 6 as seen from the left side of FIG. 6 looking in the direction of the arrow;

FIG. 10 is an exploded perspective view showing both the removal and the replacement of the needle cap for the needle that is inserted into the body of the patient;

FIG. 11 is a fragmentary longitudinal sectional view showing the hypodermic assembly inserted into a patient and with the evacuated sample receiving tube in place in the cylinder prior to needle penetration of the septum seal of the tube; and FIG. 12 is a view similar to FIG. 11 but showing the evacuated tube receiving a fluid sample.

Throughout the various figures of the drawings the same reference numerals are used to designate the same or similar parts.

DETAILED DESCRIPTION OF THE PRESENTLY PREFERRED EMBODIMENT

Figure 1:
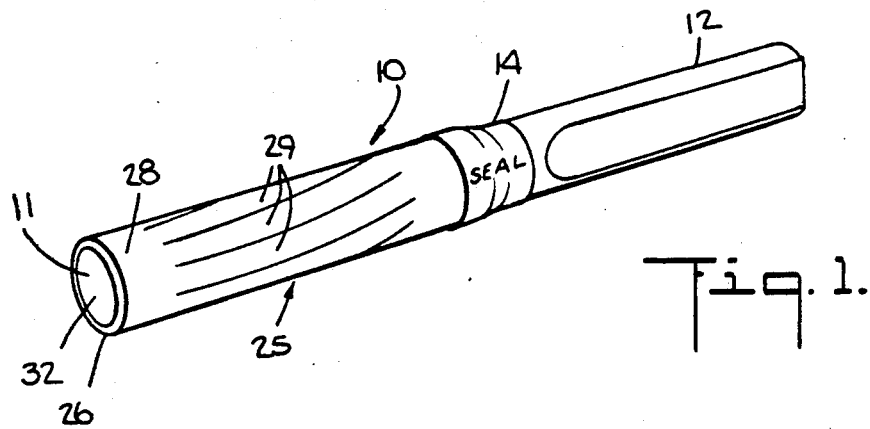
FIG. 1 is a perspective view of a double pointed hypodermic needle assembly embodying the present invention with caps enveloping the needles and joined by a sealing band.
Figure 2:
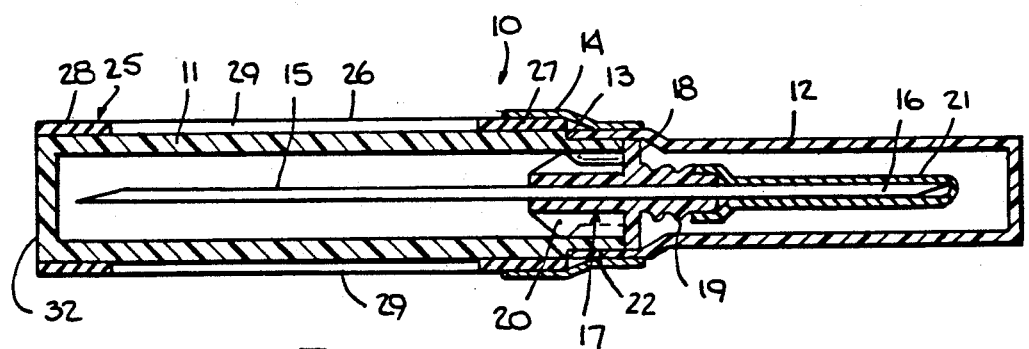
FIG. 2 is a longitudinal sectional view of the assembly of FIG. 1.

Referring to the drawings, and particularly to FIGS. 1 to 4, there is shown, designated generally by the reference numeral 10, a double pointed multiple sample hypodermic needle packaged within a sealed enclosure consisting of first and second caps 11 and 12 with their junction 13 covered by a paper sealing band 14. First and second hollow needles, 15 and 16, project in opposite directions along a common longitudinal axis from an intermediate body structure 17. The body structure 17 has a generally centrally located radial flange 18, an externally threaded extension 19 on one side of the flange 18, and a cap-engaging extension 20 on the other side of the flange 18. The first cap 11 encloses the hollow needle 15 and engages the cap engaging extension 20, which is fluted as seen in FIG. 10, while the second cap 12 encloses the hollow needle 16 and the externally threaded extension 19 and telescopes over the radial flange 18 and over an area 22 at the open end of cap 11 that has a reduced outside diameter equal to that of the flange 18. The inside diameter of the mouth 23 of the cap 12 is dimensioned to make a snug but sliding fit over flange 18 and area 22. The reduced diameter area 22 terminates at a shoulder 33 on cap 11 (see FIGS. 3 and 4) which is engaged by the end of cap 12 and defines the juncture 13. Covering needle 16 is an elastomeric pierceable self-sealing sheath 21. The needle assembly described so far represents the prior art and does not constitute an independent part of the present invention.

The invention involves the finger guard 25 consisting of a tubular element or sleeve 26 of flexible needle-puncture-resistant material having first and second circumferentially continuous end sections, 27 and 28, joined by a plurality of longitudinally extending circumferentially contiguous strips 29 which strips, when the end sections 27 and 28 are urged axially toward one another, project radially, as best seen in FIGS. 6 to 9, to form an umbrella-like structure 30. The tubular element 26 is disposed concentrically about the tubular cap 11, which cap has an open end 31 (see FIG. 10) and a closed end 32. The end section 27 of the sleeve 26 is secured to the cap 11 in the vicinity of the open end 31, that is, adjacent the shoulder 33 bordering the reduced diameter area 22.

Figure 3:
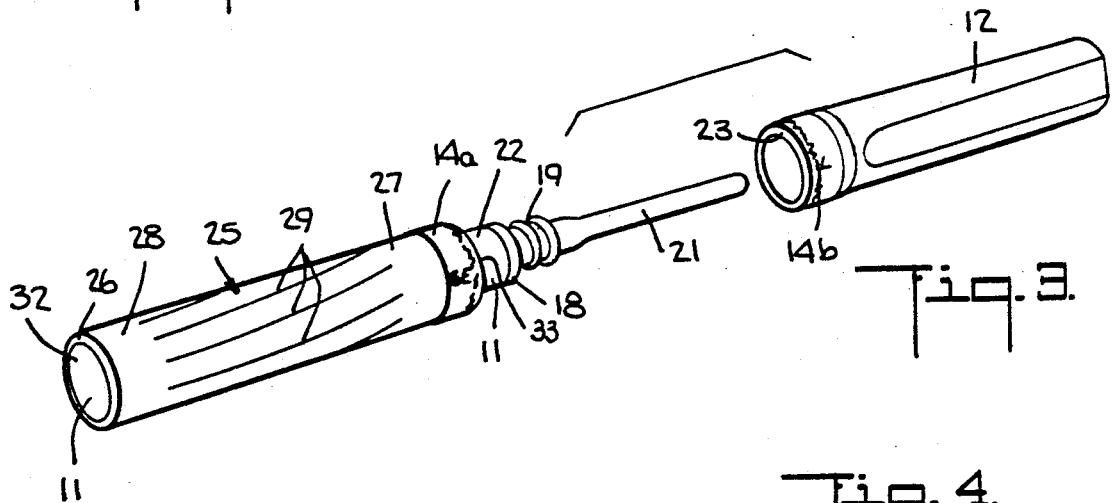
FIG. 3 is an exploded perspective view showing removal of one of the caps exposing a needle sheathed in a pierceable self-sealing elastomeric sheath.
Figure 4:
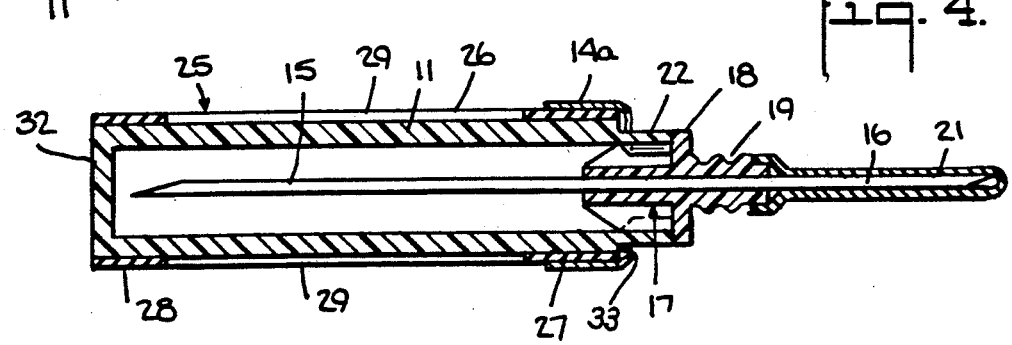
FIG. 4 is a longitudinal sectional view, similar to FIG. 2, but with the cap removed as shown in FIG. 3.
Figure 5:
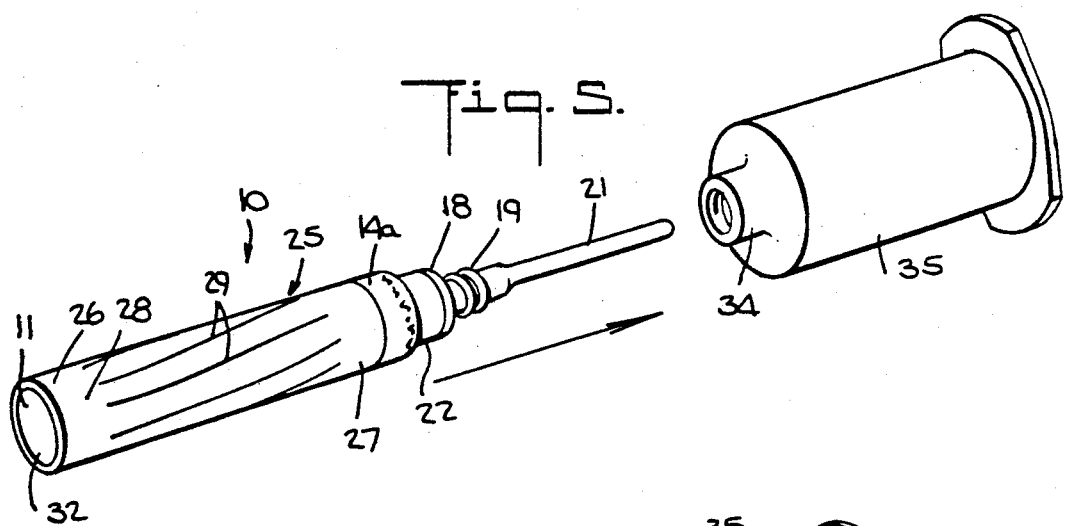
FIG. 5 is a perspective view showing the uncapped assembly of FIGS. 3 and 4 being inserted into the tube-receiving cylinder.
Figure 6:
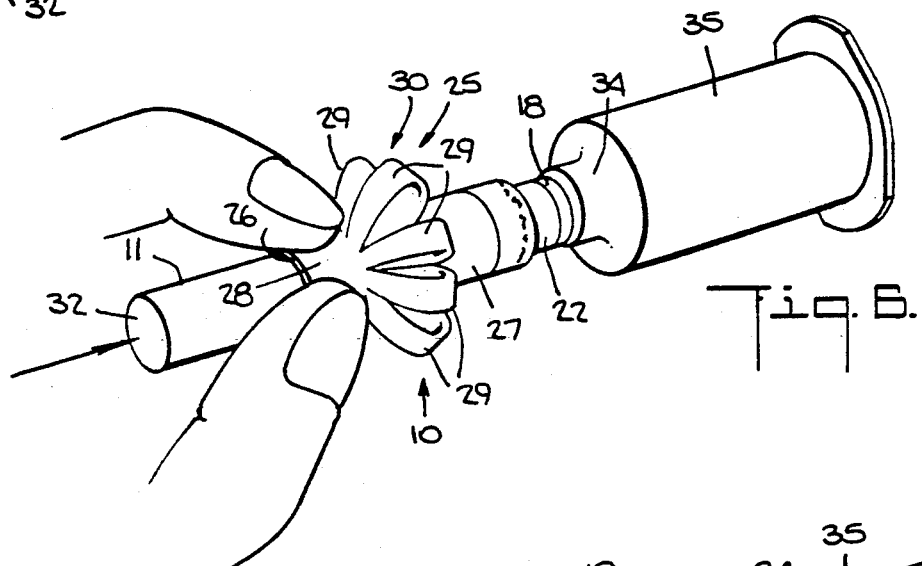
FIG. 6 is a perspective view showing the formation of the radially expanded guard during assembly of the needle and cylinder, here as a result of axial movement.
Figure 8:
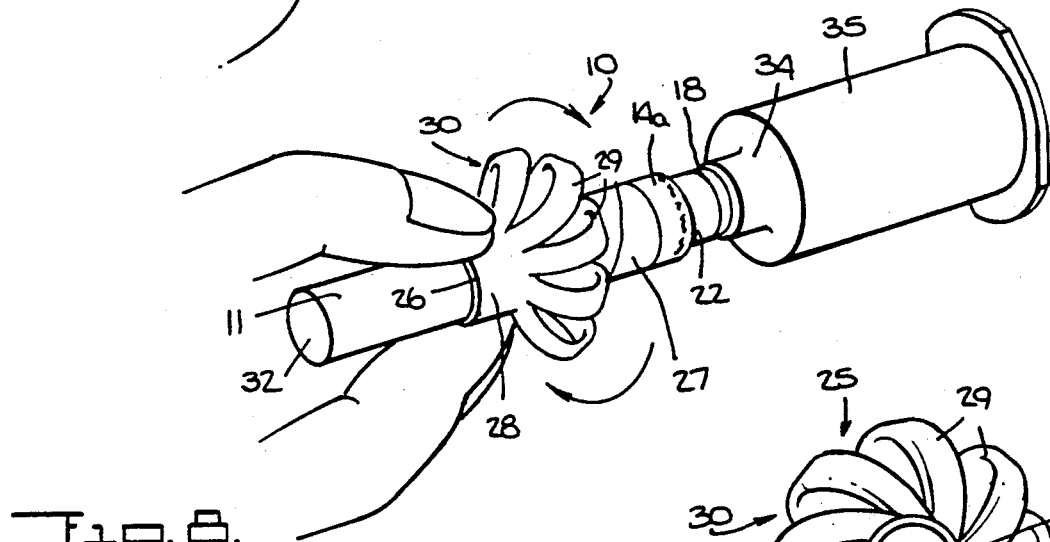
FIG. 8 is a view similar to FIG. 6 but showing further formation of the radially expanded guard by relative rotation during threaded engagement of the needle assembly and cylinder.
Figure 9:
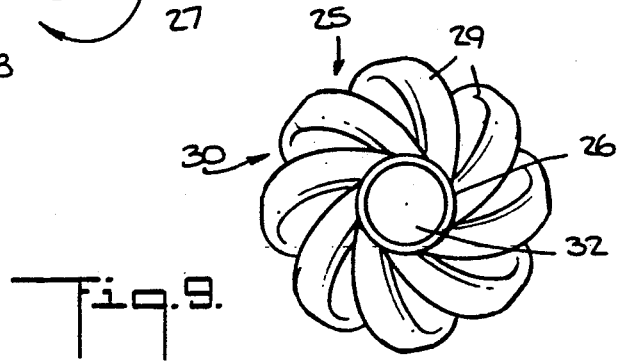
FIG. 9 is a view similar to FIG. 7 but of the guard as shown in FIG. 8.

When using the hypodermic needle 10 the sleeve element 26 is gripped with the fingers of one hand while the cap 12 is gripped by the fingers of the other hand. Through a combination of relative counterrotation and axial separation, the seal 14 is broken and the cap 12 removed exposing the sheathed needle 16 as shown in FIG. 3. Next, gripping the sleeve element 26 near or at the end section 28, the needle 16 is inserted, as shown in FIG. 5, into the internally threaded boss 34 at the base of cylinder 35. The threaded extension 19 is engaged with the threads in boss 34 and threadedly assembled. While rotating the needle 10 to engage the mating threads, the section 28 of sleeve element 26 can be urged along cap 11 toward the stationary or fixed section causing the strips 29 to buckle and project radially outwardly.

As seen in FIGS. 1, 3 and 5, the strips 29 are formed along helical lines. Because of this helical disposition, the "petals" 29 formed during the step illustrated in FIG. 6, produce a slightly fanned array as illustrated in FIG. 7. However, as clearly seen in FIG. 7, the guard has appreciable gaps in the spaces between the strip-petals 29. To eliminate these gaps, the end section 28 of sleeve element 26 should be rotated in the clockwise direction, the same direction used to engage the threads, until the petals assume the condition shown in FIG. 9. At this point the cap 11 can be removed, as seen in FIG. 10, to expose needle 15 which can then be inserted into the patient as illustrated in FIG. 11. Also, as shown in FIG. 1, the evacuated sample receiving tube 36, closed by septum 37, is being inserted into cylinder 35. As shown in FIG. 12, the tube 36 has been inserted fully into cylinder 35 with the sheath 21 displaced by septum 37, needle 16 penetrating septum 37, and a fluid sample entering tube 36.

When sampling is complete and the last tube 36 removed from engaging needle 16, the needle 15 is withdrawn from the patient and the cap 11, with guard 25 expanded, is returned over needle 15 to engage extension 20. As illustrated, the expanded structure 30 formed by guard 25 protects the fingers of the operator from being accidentally stuck by the now contaminated needle 15.

The previously described procedure is now reversed and the needle assembly 10 is separated from cylinder 35 as shown in FIG. 5. At this stage the sheath 21 has re-covered the needle 16. The cap 12 can be replaced and the assembly disposed of in the normal manner after the sleeve 26 has been restored to its initial condition as shown in FIG. 1.

It is presently contemplated that the element 26 be fabricated from a synthetic polymeric material such as polypropylene, polystyrene (medium or high impact), polyethylene, or vinyl or the like. These materials are likely to experience some set when formed into the expanded guard 30 and, consequently, may bulge slightly when the element 26 is extended to eliminate the structure 30 although this is not illustrated in the drawings.

Although the guard 25 has been illustrated with element 26 having eight strips 29, it is believed that as few as four strips can be used. The number of strips will be coordinated with the diameter of the cap 11 and with the material from which element 26 is fabricated. At this time it is not believed necessary to set limits for the thickness of the element 26. The controlling criteria is that the element 26 be sufficiently flexible to form the "umbrella" 30. Similar considerations will determine the helical angle employed for the strips 29.

Having described the present invention with reference to the presently preferred embodiment thereof, it is to be understood that various changes in construction are contemplated as will occur to those skilled in the subject art without departing from the true spirit of the invention as defined in the appended claims.

What is claimed is:

1. A finger guard comprising a tubular element of flexible needle-puncture-resistant material having first and second circumferentially continuous end sections joined by a plurality of longitudinally extending circumferentially contiguous strips which strips, when said end sections are urged axially toward one another, project radially to form an umbrella-like structure, said tubular element being disposed concentrically about a tubular cap for a hollow hypodermic needle which cap has an open end and a closed end, said first end section being secured to said cap in the vicinity of said open end thereof and said second end section being movable relative to said cap.

2. A finger guard according to claim 1, wherein said strips extend along adjacent helical paths all having the same helix angle.

3. A finger guard for a double pointed multiple sample hypodermic needle assembly wherein said needle assembly has first and second hollow needles projecting in opposite directions along a common longitudinal axis from an intermediate body structure which body structure has a generally centrally located radial flange, an externally threaded extension on one side of said flange, and a cap-engaging extension on the other side of said flange; a first cap enclosing said first hollow needle and engaging said cap engaging extension; and a second cap enclosing siad second hollow needle and said externally threaded extension and telescoped over said radial flange; said finger guard comprising a tubular element of flexible needle-puncture-resistant material having first and second circumferentially continuous end sections joined by a plurality of longitudinally extending circumferentially contiguous strips which strips, when said end sections are urged axially toward one another, project radially to form an umbrella-like structure, said first end section being secured about and to said first cap in the vicinity of the open end of said first cap with said second end section being axially slidable and rotatable relative to said first cap.

* * * * *